United States Patent [19]

Flagg

[11] 4,263,220
[45] Apr. 21, 1981

[54] ALKYLENE DICYANATES

[75] Inventor: Edward E. Flagg, Midland, Mich.

[73] Assignee: The Dow Chemical Company, Midland, Mich.

[21] Appl. No.: 118,166

[22] Filed: Feb. 4, 1980

Related U.S. Application Data

[63] Continuation-in-part of Ser. No. 10,452, Feb. 2, 1979, abandoned.

[51] Int. Cl.$^3$ ............................................. C07C 122/00
[52] U.S. Cl. ........................... 260/453 AL; 260/453 P
[58] Field of Search ....................... 260/453 AL, 453 P

[56] References Cited

U.S. PATENT DOCUMENTS

| | | | |
|---|---|---|---|
| 3,017,420 | 1/1962 | Schaeffer | 260/453 P |
| 3,107,261 | 10/1963 | Gerber et al. | 260/453 P |
| 3,553,244 | 1/1971 | Grigat et al. | 260/453 P |
| 3,681,292 | 8/1972 | Loudas et al. | 260/453 AL |
| 3,733,349 | 5/1973 | Loudas et al. | 260/453 AL |
| 3,740,398 | 6/1973 | Grigat et al. | 260/453 AL |
| 3,755,402 | 8/1973 | Grigat et al. | 260/453 AR |
| 3,962,255 | 6/1976 | Chalmers | 260/239.3 R |
| 4,085,137 | 4/1978 | Mitsch | 260/453 AL |

OTHER PUBLICATIONS

Kauer et al, *J. Am. Chem. Soc.*, vol. 86, 4732 (1964).
Grigat et al, *Chem. Ber.*, vol. 97, 3012 (1964).
Jensen et al, *Acta Chem. Scand.*, 18, 826 (1964).
Jensen et al, *Acta. Chem. Scand.*, 19, 438 (1965).
Grigat et al, *Angew. Chem. Inter. Ed.*, vol. 6, No. 3, p. 206 (1967).

*Primary Examiner*—Dolph H. Torrence
*Attorney, Agent, or Firm*—Douglas N. Deline

[57] ABSTRACT

New and useful aliphatic multifunctional cyanate compounds are prepared by the reaction of thallium(I) salts of polyols with cyanogen chloride. The compounds are useful for common reactions known for multifunctional cyanates including rearrangement into the corresponding isocyanate and then formation of polymers or use as cross-linking agents.

2 Claims, No Drawings

ALKYLENE DICYANATES

CROSS-REFERENCE TO RELATED APPLICATION

This is a continuation-in-part of copending application Ser. No. 010,452, filed Feb. 2, 1979, abandoned.

BACKGROUND OF THE INVENTION

This invention comprises novel aliphatic dicyanate and multifunctional aliphatic cyanate compounds. The following complex, sterically hindered aliphatic dicyanate has been prepared by the reaction of the corresponding sodium or lithium alkoxide with cyanogen chloride.

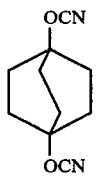

This method has not been successfully adopted to produce low molecular weight straight chain aliphatic dicyanates, but rather only complex, sterically hindered compounds like the above.

I know of no reported successful production of straight chain aliphatic dicyanate or multifunctional aliphatic cyanate compounds prior to my discovery of the instant invention.

SUMMARY OF THE INVENTION

The compounds of the present invention may be liquids or solids depending on the nature of the aliphatic moiety contained in each compound. One such multifunctional cyanate, 1,6-dicyanatohexane, is a viscous liquid at normal room temperature. The compound isomerizes to form 1,6-diisocyanatohexane upon prolonged retention at such normal room temperature. The other compounds comprising this invention also are useful in forming the corresponding isocyanato isomers. The isomers may subsequently be used to form polymers and cross-linking agents.

DETAILED DESCRIPTION OF THE INVENTION

The preparation of the new compounds of the invention may be carried out according to the following process. A thallium(I) salt of an aliphatic diol is first prepared by alkoxide exchange between a corresponding aliphatic diol and thallium(I) ethoxide according to well-known techniques in the art. The resulting thallium(I) salt of the corresponding aliphatic diol is then reacted with cyanogen chloride preferably in an inert solvent. Diethyl ether is a preferred solvent for use in this reaction, but other non-reactive solvents may also be used. Other acceptable solvents for use in producing the compounds of this invention may be determined by normal methods of chemical experimentation. The thallium(I) alkoxide reactant or a mixture of this reactant with the inert solvent is controllably added with stirring to the reaction vessel containing cyanogen chloride in an inert solvent while maintaining the reaction mixture at a temperature no greater than about 25° C. Following completion of the addition of the thallium(I) alkoxide salt, the mixture can be agitated for an additional period of time, if desired, although this is not critical. As the reaction proceeds an insoluble halide salt is formed.

The aliphatic thallium(I) alkoxide salts suitable for forming the compounds of this invention are the thallium(I) salts of alkylene diols. Preferred are $C_{2-6}$ alkylene diols which upon reaction produce the corresponding $C_{2-6}$ alkylene dicyanates. A highly preferred dicyanate is 1,6-dicyanatohexane.

The amounts of reactants to be employed are not critical, some of the desired compound is formed when employing the reactants in any proportions. However, the most efficient utilization of reactants dictates that about two moles of cyanogen chloride should be combined with each mole of thallium (I) alkoxide.

The reaction proceeds under pressures of a wide range, however, no particular advantage ordinarily results from the use of subatmospheric pressure or superatmospheric pressure; therefore, the preparation ordinarily is carried out at atmospheric pressure.

The product is recovered from the reaction mass by conventional means, as for example by vacuum distillation. Other methods of recovery may also be known to one skilled in the art. The recovered product may be further purified, if so desired, by conventional techniques known to one skilled in the art, such as, recrystallization if a solid, or fractionation of the product if a liquid.

SPECIFIC EMBODIMENTS OF THE INVENTION

Example I—1,6-Dicyanatohexane

Dithallium(I) 1,6-hexanedioxide was prepared by reaction of 1,6-hexanediol with thallium(I) ethoxide. This dithallium salt was insoluble in diethyl ether solvent, however, a measured amount of the salt was added with concomitant stirring to a solution of cyanogen chloride in diethyl ether contained in a 500 ml three-necked flask. The flask was equipped with a mechanical stirrer and a dry ice reflux trap. Temperature during the reaction was maintained at or below about 25° C. The reaction was continued until substantially all the solid dithallium(I) alkoxide salt was consumed. After completion of the reaction a viscous liquid remained after solvent removal from the reaction mass. Analysis of the liquid by common oxidation techniques provided the following results:

| $[CH_2CH_2CH_2(OCN)]_2$ | % C | % H | % N | C/H/N Ratio |
|---|---|---|---|---|
| calculated | 57.1 | 7.2 | 16.7 | 4/6/1 |
| found | 53.0 | 7.9 | 15.2 | 4/7/1 |

Analysis by infrared absorption spectroscopy and nuclear magnetic resonance spectroscopy gave results indicating both 1,6-dicyanatohexane and 1,6-diisocyanatohexane were present along with a small quantity of oligomer.

I claim:
1. A $C_{2-6}$ alkylene dicyanate compound.
2. A compound as defined in claim 1 which is 1,6-dicyanatohexane.

* * * * *